(12) United States Patent
Grainger et al.

(10) Patent No.: US 8,063,106 B2
(45) Date of Patent: Nov. 22, 2011

(54) APOE MIMETIC AGENTS

(75) Inventors: David J. Grainger, Cambridge (GB); David John Fox, Banbury (GB)

(73) Assignee: TCP Innovations Limited, Cambridge (GB)

( * ) Notice: Subject to any disclaimer, the term of this patent is extended or adjusted under 35 U.S.C. 154(b) by 186 days.

(21) Appl. No.: 12/064,117

(22) PCT Filed: Aug. 9, 2006

(86) PCT No.: PCT/GB2006/002988
§ 371 (c)(1),
(2), (4) Date: Aug. 18, 2008

(87) PCT Pub. No.: WO2007/020386
PCT Pub. Date: Feb. 22, 2007

(65) Prior Publication Data
US 2009/0221713 A1 Sep. 3, 2009

(30) Foreign Application Priority Data
Aug. 19, 2005 (GB) .................. 0517090.7

(51) Int. Cl.
| A01N 37/18 | (2006.01) |
|---|---|
| A01N 37/52 | (2006.01) |
| A61K 31/16 | (2006.01) |
| A61K 31/155 | (2006.01) |
| C07C 233/00 | (2006.01) |
| C07C 235/00 | (2006.01) |
| C07C 237/00 | (2006.01) |
| C07C 239/00 | (2006.01) |
| C07C 277/00 | (2006.01) |
| C07C 279/00 | (2006.01) |

(52) U.S. Cl. ........ 514/626; 514/634; 514/636; 564/197; 564/240; 564/241

(58) Field of Classification Search .......... 514/636, 514/634, 740, 626; 564/225, 230, 243, 197, 564/240, 241
See application file for complete search history.

(56) References Cited

U.S. PATENT DOCUMENTS
| 4,415,492 A | 11/1983 | De Weck et al. |
|---|---|---|
| 5,561,107 A | 10/1996 | Jaynes et al. |
| 2004/0039543 A1 | 2/2004 | Keck |

FOREIGN PATENT DOCUMENTS
| EP | 0047197 A1 | 3/1982 |
|---|---|---|
| EP | 1502949 A1 | 2/2005 |
| WO | WO-9965506 A2 | 12/1999 |
| WO | WO-0011022 A1 | 3/2000 |
| WO | WO-03018619 A2 | 3/2003 |
| WO | WO-03026479 A2 | 4/2003 |
| WO | WO-03048383 A2 | 6/2003 |
| WO | WO-2005025607 | 3/2005 |
| WO | WO-2005072295 A2 | 8/2005 |

OTHER PUBLICATIONS

Gobec et. al., Bioorganic and Medicinal Chemistry Letters, 2004, Elsevier, vol. 14, pp. 3933-3936.*
Lin et. al., Bioorganic and Medicinal Chemistry Letters, 1999, Elsevier, vol. 9, pp. 2747-2752.*
"International Application No. PCT/GB2006/002988 International Preliminary Report on Patentability mailed Feb. 28, 2008", 15 pgs.
"International Application No. PCT/GB2006/002988 International Search Report and Written Opinion mailed Feb. 8, 2007", 22 pgs.

* cited by examiner

*Primary Examiner* — Shengjun Wang
*Assistant Examiner* — Sarah Pihonak
(74) *Attorney, Agent, or Firm* — VLP Law Group LLP; Richard G. A. Bone

(57) ABSTRACT

The invention provides low molecular weight apoE mimetic agents suitable for preparing a medicament to treat autoimmune, inflammatory or neurodegenerative disease, $(X)_a$-L-$(X)_b$(Formula (I)) wherein each X is a (potentially different) chemical moiety bearing a positive charge at physiological pH a and b are, independently, numbers between 3 and 6; and L is a linker.

Cmpnd A

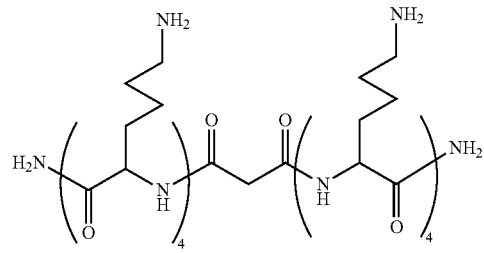

Cmpnd B

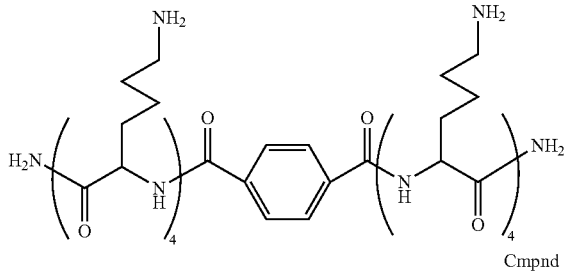

Cmpnd C

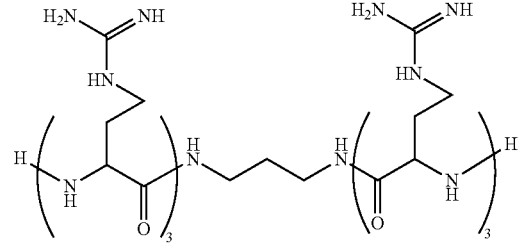

2 Claims, 1 Drawing Sheet

APOE MIMETIC AGENTS

RELATED APPLICATIONS

Figure 1:
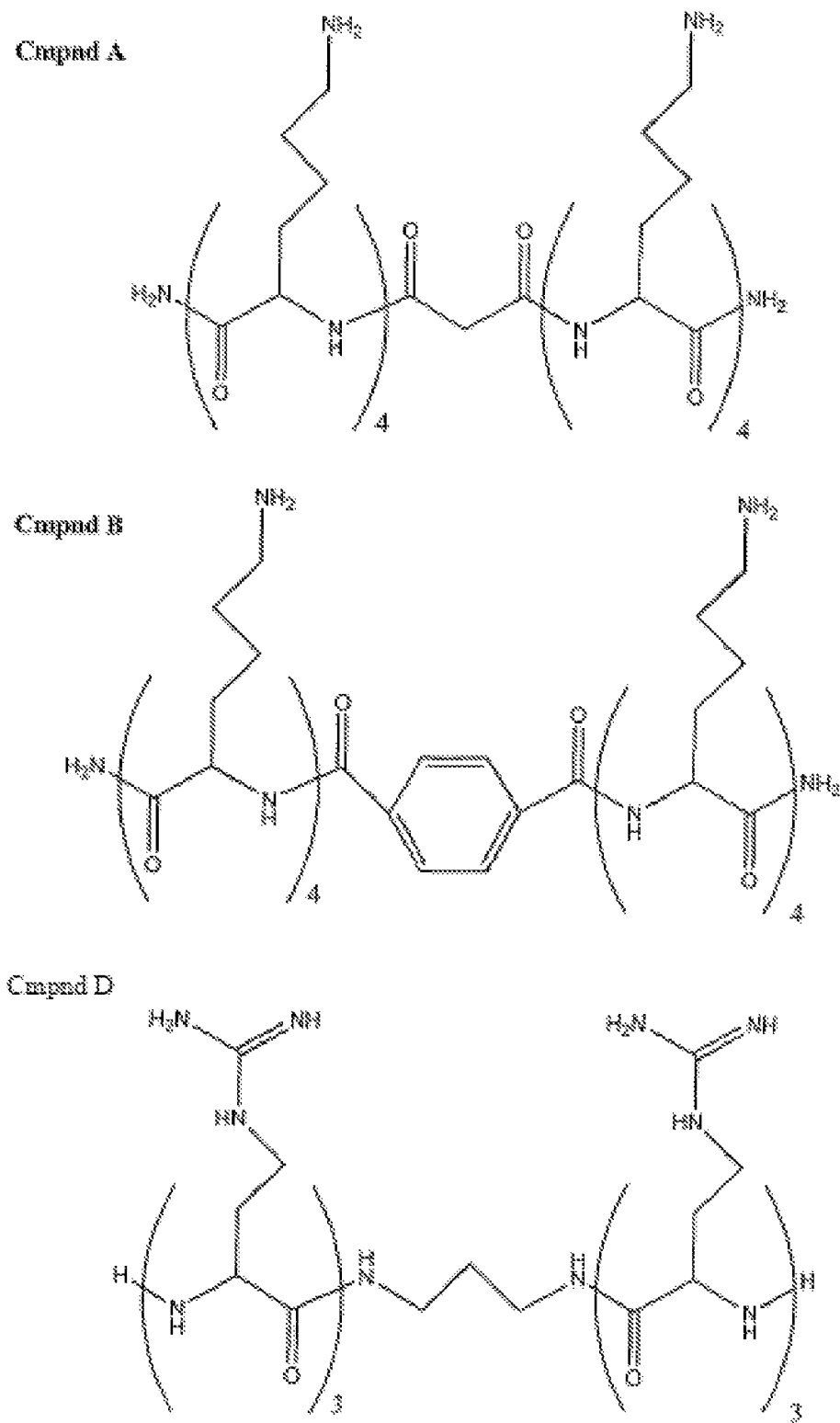

This application is a U.S. National Stage Filing under 35 U.S.C. 371 from International Application Number PCT/GB2006/002988, filed Aug. 9, 2006 and published in English as WO 2007/020386 A2 on Feb. 22, 2007, which claims the benefit of GB Application Serial Number 0517090.7, under 35 U.S.C. 119, which applications and publication are incorporated herein by reference in their entirety.

The invention relates to the use of dimeric oligocationic derivatives for preparing a medicament intended to prevent or treat inflammatory or neurodegenerative disorders.

Apoptosis is the name give to a physiological process whereby unwanted cells in the body commit to programmed cell death. It is an important process during development (where, for example, apoptosis of cells in the hand between the digits results in the separation of the fingers) and also in the adult (where, for example, apoptosis is the major mechanism whereby white blood cells are cleared from a site of inflammation during the resolution phase when they are no longer required).

During apoptosis, the cell contents are carefully packaged up into membrane bound vesicles. This is essential to prevent the intracellular contents spilling out (as they do in the uncontrolled cell death, called necrosis, that occurs in response, for example, to many chemical toxins). When the intracellular contents are accidentally spilled this can have a number of harmful consequences: locally, powerful enzymes such as proteases which were previously kept sequestered are now free to damage multiple substrates; systemically, the immune system encounters proteins normally shielded inside the cells. This latter interaction is now thought to play an important role in the development of autoimmune disease, since repeated exposure to intracellular antigens can lead to the development of autoantibodies. Apoptosis limits these problems by packaging away the cell debris during programmed cell death.

But what becomes of the membrane-bound vesicles of cellular debris? An essential function of the immune system is to ingest these remnants of apoptotic cells, and to degrade the components to basic building blocks that can be recycled into cellular metabolism. Efficient clearance of apoptotic remnants is therefore an essential physiological function, and any failure of the process can lead to accumulation of uncleared cell debris.

Two major factors therefore determine the amount of uncleared cell debris in a tissue: the rate of cell death and the rate of remnant clearance. Exposures that increase the rate of cell death (such as traumatic tissue injury, for example) will increase the pressure on the remnant clearance mechanisms. If there is insufficient clearance capacity, remnants will accumulate at least in the short term. Thus, if different individuals have different remnant clearance rates or capacities, either due to genetic or environmental factors, then they will show greater propensity to accumulate uncleared cell debris in various tissues both under normal conditions, but more likely under stressor conditions such as traumatic tissue injury.

Failure to clear the debris has a further important consequence beyond local and systemic exposure to intracellular enzymes and antigens. White blood cells, and in particular phagocytes such as macrophages, are responsible for clearing the debris; so accumulated debris acts to stimulate recruitment of macrophages. If the phagocytes so recruited are inefficient at their clearance duties, then a larger number of tissue macrophages will be required to keep on top of the debris clearance. A higher density of tissue macrophages results in elevated levels of local and systemic pro-inflammatory mediators and a persistent pro-inflammatory state ensues.

We have recently described a novel mechanism that regulates the efficiency of remnant clearance by macrophages both in vitro and in vivo. We demonstrated that the protein apoE signals to macrophages in some way to increase their efficiency at taking up unwanted cell debris. Consequently, mice with a deletion in the apoE gene demonstrated an increased tendency to accumulate apoptotic cell remnants in a wide range of tissues (including liver, lung, skin and brain), and an accompanying pro-inflammatory state with a higher density of tissue macrophages in each of these tissues (Grainger et al; *Journal of Immunology* (2004) 173:6366). Treatment with the apoE protein restored normal clearance rates and capacity, and alleviated the pro-inflammatory state.

Similar pathways are likely to be operative in humans. ApoE exists in three allelic variants, designated apoE2, E3 and E4. The presence of apoE4, in particular, is associated with increased prevalence of a variety of diseases associated with the chronic degeneration of normal tissue architecture. For example, individuals with at least one allele encoding E4 are more than twice as likely to develop Alzheimer's Disease before their $65^{th}$ birthday. Differential ability to stimulate apoptotic cell clearance is likely to be one of the mechanisms underlying this powerful genetic association with disease.

Consequently, apoE mimetics are a potential new therapeutic option for preventing or curing diseases where inefficient clearance of cell debris is a component of the pathogenic mechanism. This likely includes autoimmune diseases, other inflammatory diseases and chronic degenerative diseases such as neurodegeneration. Indeed, any disease where rates of cell death are increased or where clearance of cell debris becomes limiting for retaining normal tissue architecture will likely be amenable to treatment with apoE mimetic agents.

Previously, we have described our discovery of the role of apoE as physiologically relevant modulator of apoptotic cell clearance (Grainger et al; *Journal of Immunology* (2004) 173:6366), and described a series of methods suitable for the identification of apoE mimetic agents useful for the treatment of indications where inefficient clearance of cell debris is a contributory pathogenic mechanism (Grainger D J; GB patent application number GB0423658.4 filed 25 Oct. 2004).

Others have previously described peptides which can mimic various functions of apoE (although not for the purpose of stimulating apoptotic cell clearance, which is likely to be mediated through different apoE:receptor interactions compared with other apoE functions). For example, Laskowitz and colleagues have described various peptides taken from the sequence of human apoE which can mimic certain functions of the whole protein (Laskowitz et al., Downregulation of microglial activation by apolipoprotein E and apoE-mimetic peptides. *Exp. Neurol.* (2001) 167:74; US patent application numbers US2002/0164789 and US2003/0077641). Dyer and colleagues have also described peptides derived from the apoE sequence which can mimic the function of the whole protein (Dyer et al., *Journal of Biological Chemistry* (1991) 266:15009; Dyer & Curtiss. *Journal of Biological Chemistry* (1991) 266:22803; Dyer et al., *Lipid Research* (1995) 36:80). Similar peptides have also been claimed by Crutcher and Harmony (U.S. Pat. No. 6,245,751 dated Jun. 12, 2001). However, none of these existing reports describe apoE mimetics other than peptides derived from the sequence of human apoE, and none describe compounds with selective activity for stimulating clearance of apoptotic cells over other functions of apoE.

Here, we describe the first family low molecular weight apoE mimetic agents suitable for preparing a medicament to treat autoimmune, inflammatory or neurodegenerative disease.

The invention provides the use of a compound of general formula (I), or a pharmaceutically acceptable salt thereof, for the preparation of a medicament intended to treat inflammatory disorder:

$$(X)_a\text{-L-}(X)_b \quad (I)$$

wherein each X is a (potentially different) chemical moiety bearing a positive charge at physiological pH a and b are, independently, numbers between 3 and 6;

and L is a linker consisting of a linear or branched alkyl moiety consisting of between 2 and 20 carbon atoms; or a disubstituted cyclopentane (either 1,2 or 1,3 substituted), cyclohexane (either 1,2, 1,3 or 1,4 substituted) or other disubstituted cycloalkane or polycycloalkane, including adamantane, decalin or bicyclooctane where each substituent is a linear or branched alkyl moiety consisting of between 0 and 10 carbon atoms; or a disubstituted aromatic ring system, including benzyl (either meta, ortho or para disubstituted), pyridinyl, coumaryl, napthalenyl and pyrimidyl, where each substituent is a linear or branched alkyl moiety consisting of between 0 and 10 carbon atoms.

Optionally, the compounds of general formula (I) may have every X moiety (on both sides of the linker, L) different from every other X moiety in the compound, provided only that each bears a positive charge at physiological pH. Such compounds might be of the general structure X1-X2-X3-L-X4-X5-X6.

Alternatively, it is also envisaged that all of the X moieties on one side of the linker, L, may be repetitions of the same moiety that bears a positive charge at physiological pH, while the X moieties on the other side of the linker, L, may be the same as this repeated X moiety, or may all be different. Such compounds might be of the general structure X1-X1-X1-L-X2-X3-X4.

Alternatively, it is also envisaged that all of the X moieties on one side of the linker, L, may be repetitions of the same moiety that bears a positive charge at physiological pH, while the X moieties on the other side of the linker, L, may also be repetitions of a different X moiety that bears a positive charge at physiological pH. Such compounds might be of the general structure X1-X1-X1-L-X2-X2-X2.

Alternatively, it is also envisaged that all of the X moieties on both sides of the linker, L, may be repetitions of the same moiety that bears a positive charge at physiological pH. Such compounds might be of the general structure X1-X1-X1-L-X2-X2-X2.

Preferably, the compounds of general formula (I) will be polyamides, according to one of the general formulae (II), (III) or (IV) below:

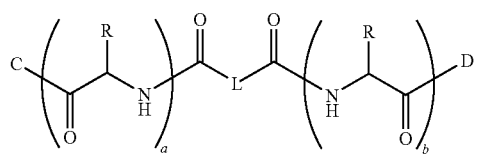

(II)

where L, a and b have the same meanings as above;

C and D are independently chosen from linear or branched alkyl, haloalkyl, hydroxyalkyl radicals or cycloalkyl or polycycloalkyl radicals containing between 0 and 10 carbon atoms, or NZZ' where Z and Z' are independently or together chosen from linear or branched alkyl, haloalkyl, hydroxyalkyl radicals or cycloalkyl or polycycloalkyl radicals containing between 0 and 10 carbon atoms;

each R is a (potentially different) chemical moiety bearing a positive charge at physiological pH.

Optionally, each R group in the molecule may be of different structure (provided only that it bears positive charge at physiological pH), or alternatively all the R groups on one, or both, sides of the linker, L, may be repetitions of the same moiety bearing positive charge at physiological pH, or alternatively all the R groups in the compound may be repetitions of the same moiety bearing positive charge at physiological pH.

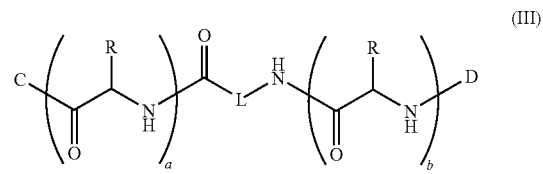

(III)

where L, a and b have the same meanings as above;

C is chosen from H, OH, linear or branched alkyl, haloalkyl, hydroxyalkyl radicals or cycloalkyl or polycycloalkyl radicals containing between 0 and 10 carbon atoms, or NZZ' where Z and Z' are independently or together chosen from H, linear or branched alkyl, haloalkyl, hydroxyalkyl radicals or cycloalkyl or polycycloalkyl radicals containing between 0 and 10 carbon atoms;

D is chosen from H, linear or branched alkyl, haloalkyl, hydroxyalkyl radicals or cycloalkyl or polycycloalkyl radicals containing between 0 and 10 carbon atoms, or COZ where Z is chosen from H, OH, linear or branched alkyl, haloalkyl, hydroxyalkyl radicals or cycloalkyl or polycycloalkyl radicals containing between 0 and 10 carbon atoms;

each R is a (potentially different) chemical moiety bearing a positive charge at physiological pH.

Optionally, each R group in the molecule may be of different structure (provided only that it bears positive charge at physiological pH), or alternatively all the R groups on one, or both, sides of the linker, L, may be repetitions of the same moiety bearing positive charge at physiological pH, or alternatively all the R groups in the compound may be repetitions of the same moiety bearing positive charge at physiological pH.

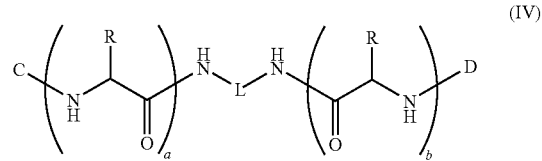

(IV)

where L, a and b have the same meanings as above;

C and D are independently chosen from H, linear or branched alkyl, haloalkyl, hydroxyalkyl radicals or cycloalkyl or polycycloalkyl radicals containing between 0 and 10 carbon atoms, or COZ where Z is chosen from H, OH, linear or branched alkyl, haloalkyl, hydroxyalkyl radicals or cycloalkyl or polycycloalkyl radicals containing between 0 and 10 carbon atoms;

each R is a (potentially different) chemical moiety bearing a positive charge at physiological pH.

Optionally, each R group in the molecule may be of different structure (provided only that it bears positive charge at physiological pH), or alternatively all the R groups on one, or both, sides of the linker, L, may be repetitions of the same moiety bearing positive charge at physiological pH, or alternatively all the R groups in the compound may be repetitions of the same moiety bearing positive charge at physiological pH.

Preferably, the compounds of formula (II), (II) or (IV) will have each R independently selected from the list of alkylamino, alkylaminoalkyl. alkylaminodialkyl or alkylaminotrialkyl, consisting of between 1 and 10 carbon atoms, including linear, branched, cyclic and polycyclic alkyl residues.

The invention also provides pharmaceutical compositions comprising, as active ingredient, a compound of general formula (I), (II), (III) or (IV) or a pharmaceutically acceptable salt thereof, and at least one pharmaceutically acceptable excipient and/or carrier By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention also provides compounds and salts thereof of general formula (I), (II), (III) or (IV).

In particular, preferred compounds of general formula (I), (II), (III) or (IV) and their salts according to any aspect of the present invention are selected from the group consisting of:
— N,N'-Bis-(5-amino-1-{5-amino-1-[5-amino-1-(5-amino-1-carbamoyl-pentylcarbamoyl)-pentylcarbamoyl]-pentylcarbamoyl}-pentyl)-malonamide (CmpdA);
— N,N'-Bis-(5-amino-1-{5-amino-1-[5-amino-1-(5-amino-1-carbamoyl-pentylcarbamoyl)-pentylcarbamoyl]-pentylcarbamoyl}-pentyl)-terephthalamide (Cmpd B)
— N,N'-Bis-(2-{2-[2-(2-Amino-5-guanidino-pentanoylamino)-5-guanidino-pentanoyl amino]-5-guanidino-pentanoylamino}-5-guanidino-pentanoyl)-1,3-diaminopropane (Cmpd C)

and the salts thereof.

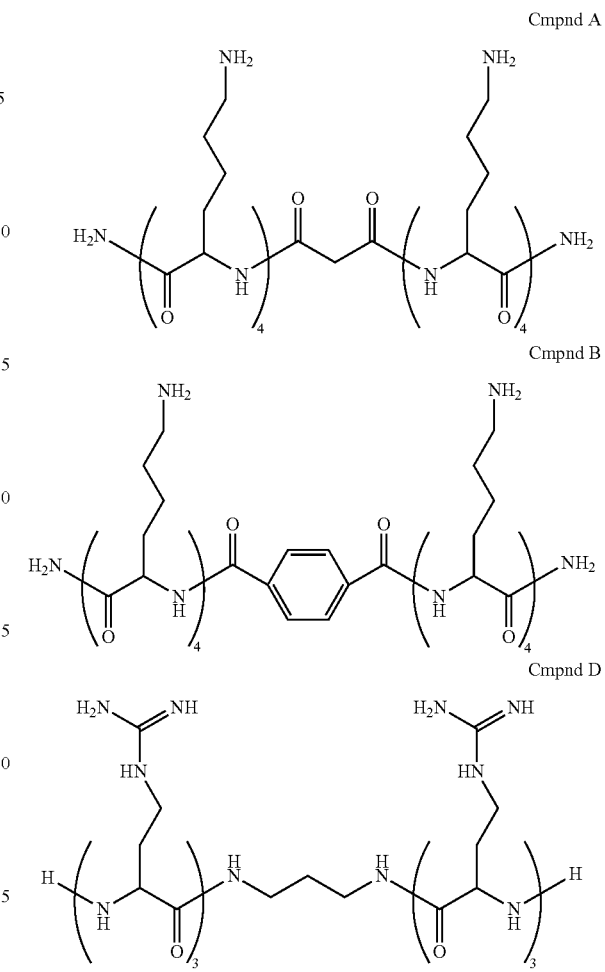

The invention includes compounds, compositions and uses thereof as defined, wherein the compound is in hydrated or solvated form.

The invention includes compounds, compositions and uses thereof as defined, wherein the compound is reacted with protecting groups that are released under physiological conditions, so as to generate derivatives which are more suitable for administration in vivo. For example, the guanidinium groups in Cmpd C could be protected as the oxime derivative, which converts to the free guanidinium group in vivo (based on the principles outlined in the development of the pro-drug Ximelogatran from the direct thrombin inhibitor Melogatran; Gustafsson et al. A new Oral Anticoagulant: the 50-year Challenge. *Nature Reviews Drug Discovery* (2004) 3:649).

The dimeric oligocationic compounds described here are the first class of functional apoE mimetics which are not simple peptides. They are relatively inexpensive to synthesise, using facile synthesis routes well known in the art; they are highly potent and effective anti-inflammatory agents. Taken together, these properties suggest that dimeric oligocationic compounds represent apoE mimetics with advantages over previously described compounds.

In comparison to the prior art, a further improvement of the present invention lies in the property of these compounds to selectively promote apoptotic cell phagocytosis, through agonist properties at the LRP family of receptors, and specifically at LRP1, over their ability to bind to and modulate LDL receptor related function. ApoE itself, and simple peptide derivatives of apoE previously known in the art either bind preferentially to LDL receptor, or else show no preference between LDL receptor and LRP. Since interaction with LDL receptor interferes with lipoprotein trafficking and metabolism, the compounds of the present invention are likely to have significantly fewer side-effects than prior art compounds.

According to this invention, inflammatory disorders intended to be prevented or treated by the compounds of general formula (I), (II), (III) or (IV) or the pharmaceutically acceptable salts thereof or pharmaceutical compositions or medicaments containing them as active ingredients include notably:

- autoimmune diseases, for example such as multiple sclerosis, rheumatoid arthritis, Crohn's disease, Grave's disease, mysethenia gravis, lupus erythromatosis, scleroderma, Sjorgren's syndrome, autoimmune type I diabetes;
- vascular disorders including stroke, coronary artery diseases, myocardial infarction, unstable angina pectoris, atherosclerosis or vasculitis, e.g., Behçet's syndrome, giant cell arteritis, polymyalgia rheumatica, Wegener's granulomatosis, Churg-Strauss syndrome vasculitis, Henoch-Schönlein purpura and Kawasaki disease;
- viral infection or replication, e.g. infections due to or replication of viruses including pox virus, herpes virus (e.g., Herpesvirus samiri), cytomegalovirus (CMV) or lentivirus;
- asthma, allergic rhinitis or chronic occlusive pulmonary disease (COPD);
- osteoporosis (low bone mineral density);
- tumor growth;
- organ transplant rejection and/or delayed graft or organ function, e.g. in renal transplant patients;
- a disorder characterised by an elevated TNF-α level;
- psoriasis;
- skin wounds;
- disorders caused by intracellular parasites such as malaria or tuberculosis;
- allergies; or According to this invention, further inflammatory disorders include:
- ALS;
- fibrosis (particularly pulmonary fibrosis, but not limited to fibrosis in the lung);
- the formation of adhesions (particularly in the peritoneum and pelvic region).
- antigen induced recall response
- immune response suppression These clinical indications fall under the general definition of inflammatory disorders or disorders characterized by elevated TNFα levels.

According to this invention, neurodegenerative disorders intended to be prevented or treated by the compounds of general formula (I), (II), (III) or (IV) or the pharmaceutically acceptable salts thereof or pharmaceutical compositions or medicaments containing them as active ingredients include notably:

- Alzheimer's disease, and other idiopathic dementias resulting from neurodegeneration;
- Parkinson's disease;
- Huntington's disease;
- Traumatic brain injury (such as head injuries resulting from a motor vehicle accident), as well as the chronic sequelae (such as impaired memory) resulting from such acute traumatic injuries Where legally permissible, the invention also provides a method of treatment, amelioration or prophylaxis of the symptoms of an inflammatory disease (including an adverse inflammatory reaction to any agent) or a neurodegenerative disease by the administration to a patient of an anti-inflammatory amount of a compound, composition or medicament as claimed herein.

Administration of a medicament according to the invention can be carried out by topical, oral, parenteral route, by intramuscular injection, etc.

The administration dose envisaged for a medicament according to the invention is comprised between 0.1 mg and 10 g depending on the type of active compound used.

According to the invention, the compounds of general formula (I), (II), (III) or (IV) can be prepared using the processes described hereafter.

Preparation of the Compounds of General Formula (I), (II), (III) or (IV)

Compounds of general formula (I) can be prepared according to general methods known to the person skilled in the art.

In general, the compounds are prepared in two steps. In the first step a short, oligocationic derivative is synthesised by oligomerising a suitable cationic monomer. For polyamide agents, such as (II), (III) or (IV), a polycationic oligopeptide can by synthesised by solid phase synthesis methods well known in the art, or else purchased directly from a wide variety of commercial suppliers (such as Bachem). Any free amino or carboxylate groups must be protected using appropriate protecting group chemistry well known in the art (for example, free amine groups can be protected using Boc or Z groups).

In the second step, the short oligocationic derivative is reacted with a difunctionalised linker to generate a dimeric oligocationic agent of the invention. For polyamide agents, such as (II), (III) or (IV), the polycationic oligopeptide is reacted with a dicarboxylic acid, a diamine or an amino acid in order to generate the agent of the invention. Such a reaction is performed under conditions well known in the art for the formation of solution phase amide bonds.

Following synthesis, any protecting groups used during the second step of the synthesis are removed using methods well known in the art.

DEFINITIONS

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 1 to 20 carbon atoms specified in respect of (inter alia) formula I is intended to include all integers between 4 and 20 and all sub-ranges of each combination of upper and lower numbers, whether exemplified explicitly or not.

As used herein, the term "comprising" is to be read as meaning both comprising and consisting of. Consequently, where the invention relates to a "pharmaceutical composition comprising as active ingredient" a compound, this terminology is intended to cover both compositions in which other active ingredients may be present and also compositions which consist only of one active ingredient as defined.

The term "peptidic moieties" used herein is intended to include the following 20 naturally-occurring proteogenic amino acid residues:

| SYMBOL: | MEANING |
|---|---|
| Ala | Alanine |
| Cys | Cysteine |
| Asp | Aspartic Acid |
| Glu | Glutamic Acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Modified and unusual amino acid residues, as well as peptido-mimetics, are also intended to be encompassed within the definition of "peptidic moieties".

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the above procedures and should in no way be considered to limit the scope of the invention.

FIGURES

FIG. 1 shows the chemical structure of examples of compounds according to the invention.

EXAMPLES

Example 1

Malonyl-di-(Lys)$_4$-amide (Cmpnd A)

The free carboxylic acid of Nα-(Nα-(Nα-(Nα-Boc-Nε-Cbz-lysyl)-Nε-Cbz-lysyl)-Nε-Cbz-lysyl)-Nε-Cbz-lysine was converted into a primary amide using ammonia and a peptide coupling agent such as PyBOP. Following removal of the Boc group with acid, the ammonium salt was then basified and coupled twice to a 1-ω-di-carboxylic acid (in this case, malonic acid) by standard methods, forming a symmetrical intermediate. The Cbz protecting groups were then removed by hydrogenolysis, to produce the required product.

Example 2

Benzene-1,4-dicarboxylic acid-di-(Lys)$_4$-amide (Cmpnd B)

The free carboxylic acid of Nα-(Nα-(Nα-(Nα-Boc-Nε-Cbz-lysyl)-Nε-Cbz-lysyl)-Nε-Cbz-lysyl)-Nε-Cbz-lysine was converted into a primary amide using ammonia and a peptide coupling agent such as PyBOP. Following removal of the Boc group with acid, the ammonium salt was then basified and coupled twice to a 1-ω-di-carboxylic acid (in this case, terephthalic acid) by standard methods, forming a symmetrical intermediate. The Cbz protecting groups were then removed by hydrogenolysis, to produce the required product.

Example 3

1,4-diaminobutane-di-(Arg)$_4$-amide

Alternatively the peptide fragments could be coupled "C-end to C-end", by related method. The carboxylic acid functional groups of two equivalents of Nα-(Nα-(Nα-Boc-N$^G$-Pbf-Arginyl)-N$^G$-Pbf-Arginyl)-N$^G$-Pbf-Arginyl)-N$^G$-Pbf-Arginine (Pbf=2,2,4,6,7-pentamethyldihydrobenzofuran-5-sulfonyl, an acid removable protecting group ref. Carpino et al. *Tetrahedron Lett.* 1993, 34, 7829 and Fields et al. *Tetrahedron Lett.* 1993, 34, 6661) was activated with a standard peptide coupling agent, such as PyBOP, and reacted with a 1-ω-di-amine (in this case, 1,4-diaminobutane) to give, after acid mediated global deprotection, the target material Pharmacological Study of the Products of the Invention
Stimulation of Macrophage Phagocytosis
Assay Principle The principle of the assay is to measure the average number of particles taken up by cultured macrophages in a fixed period of time. Typically, fluorescently labelled particles are used, so that the number of particles ingested can be readily determined by flow cytometry. The principles of this assay were previously described in detail elsewhere (Grainger D J; GB patent application number GB0423658.4 filed 25 Oct. 2004).

Materials

CellTracker Green dye was obtained from Molecular Probes Inc. Cell culture plasticware was obtained from Nunc. Fetal calf serum, cell culture media and miscellaneous chemicals were obtained from Sigma.

Test Protocol (a) Exposure of cultured macrophages to various concentrations of the putative apoE mimetic. Macrophages are generated by the in vitro differentiation of the human myelomonocytic cell line THP-1. THP-1 cells are plated in tissue culture wells at approximately 10$^5$ cells per well, and exposed to phorbol myristyl acetate (PMA) at 200 nM for 24 hours to induce differentiation into macrophages. After 24 hours, successful differentiation is confirmed by the adherence of the macrophages to the plastic (and also by the upregulation in CD14 expression). Any undifferentiated cells (which are not adherent) are washed away. The putative apoE mimetic is then added at suitable concentrations to a range of replicate wells, typically between 10 pM and 10 mM, more typically between 1 nM and 100 μM. The apoE mimetic may be added in any suitable biologically compatible buffer known in the art, most preferably in aqueous buffered salt solution such as PBS. Typically, triplicate wells of cultured macrophages are exposed to different concentrations of apoE mimetic (including control wells exposed to the vehicle alone). The cells are then left exposed to the apoE mimetic for 2 hours at 37° C., before preceeding to the next step.

(b) Exposure of the culture macrophages to apoptotic cells under conditions suitable for phagocytosis. Apoptotic cells are obtained by withdrawal of serum for 24 hours from primary lymphocytes, cultured for 1 to 4 days from human peripheral blood (originally isolated by density gradient centrifugation). For the period in which serum is withdrawn a fluorescent dye, CellTracker Green, is added to the medium at 100 μg/ml final concentration to label the lymphocytes as they become apoptotic. Typically, more than 50% of the cells in the population to be used are undergoing apoptotis defined by staining with labelled Annexin V. $10^6$ apoptotic cells are added to each replicate well of macrophages, while the apoE mimetic remains present in the culture medium throughout the time when phagocytosis is occurring. The macrophages are then incubated at 37° C. for 1 hour, during which time phagocytosis occurs. Note that under these experimental conditions a maximum of 10% of the added apoptotic cells are ingested by the macrophages, ensuring that availability of particulates for uptake never becomes limiting.

(c) Detection of the number of apoptotic cells which have been taken up into the macrophages by phagocytosis. At the end of the phagocytosis period, the cells are washed three times vigorously with ice cold PBS (to remove any particulates bound to the cell surface rather than internalised). The labelled apotoic cells are then identified and counted by detecting the fluorescent label under appropriate conditions by microscopy. The number of ingested apoptotic cells is then counted, together with the total number of macrophages performing the phagocytosis. At the end of the experiment, typically the extent of phagocytosis occurring in a defined period (as an estimate of the average rate of phagocytosis) is expressed as the number of thymocytes taken up per macrophage per hour. Typically, this value ranges of 2 to 4 in wild-type cells in the absence of an apoE mimetic. The effect of the apoE mimetic is then expressed as the fold-change in this value compared to control cells not exposed to the apoE mimetic.

Results

The compounds of examples 1 to 3 were tested and were shown to stimulate the rate of phagocytosis in this test by at least 2-fold. The ED50 for the effect was <10 μM.

The invention claimed is:
1. A compound of formula (IV):

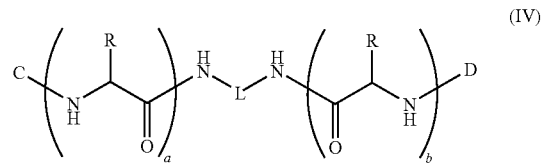

where L is a linear alkyl moiety consisting of 4 carbon atoms;
a and b are both 4;
C and D are both H; and
each R is 1-(3-guanidino-propyl).

2. A pharmaceutical composition comprising, as active ingredient, a compound of formula (IV) or a pharmaceutically acceptable salt thereof, and at least one pharmaceutically acceptable excipient and/or carrier:

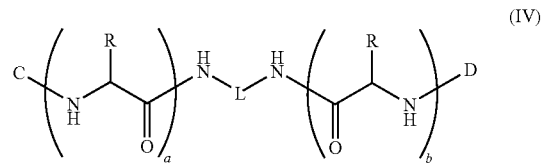

where L is a alkyl moiety consisting of 4 carbon atoms;
a and b are both 4;
C and D are both H; and
each R is 1-(3-guanidino-propyl).

* * * * *